United States Patent [19]

Isogai et al.

[11] 4,289,911
[45] Sep. 15, 1981

[54] PROCESS FOR PRODUCING METHYLISOBUTYLKETONE

[75] Inventors: Nobuo Isogai; Takashi Okawa; Natsuko Wakui, all of Niigata, Japan

[73] Assignee: Mitsubishi Gas Chemical Company, Inc., Tokyo, Japan

[21] Appl. No.: 157,539

[22] Filed: Jun. 9, 1980

[30] Foreign Application Priority Data

Jun. 13, 1979 [JP] Japan .................. 54-74418

[51] Int. Cl.$^3$ .................. C07C 45/45; C07C 29/136
[52] U.S. Cl. .................. 568/396; 568/387; 568/881
[58] Field of Search .................. 568/396; 568/387, 881

[56] References Cited

U.S. PATENT DOCUMENTS

| | | | |
|---|---|---|---|
| 3,130,237 | 4/1964 | Wald | 568/396 |
| 3,316,303 | 4/1967 | Mertzweiller et al. | 568/396 |
| 3,379,766 | 4/1968 | Hwang et al. | 568/396 |
| 3,454,644 | 7/1969 | Dewhirst | 568/396 |
| 3,666,816 | 5/1972 | Takagi et al. | 568/396 |
| 3,829,495 | 8/1974 | Milutani | 568/396 |
| 3,953,517 | 4/1976 | Schmitt et al. | 568/396 |

FOREIGN PATENT DOCUMENTS

| | | | |
|---|---|---|---|
| 1193931 | 3/1966 | Fed. Rep. of Germany | 568/396 |
| 1936203 | 7/1968 | Fed. Rep. of Germany | 568/396 |
| 2022365 | 11/1970 | Fed. Rep. of Germany | 568/396 |

OTHER PUBLICATIONS

Nissen, Chem. Abst., vol. 88, #22397d (1978).
Mizutani et al., Chem. Abst., vol. 88, #169598d (1978).

*Primary Examiner*—Natalie Trousof
*Assistant Examiner*—James H. Reamer
*Attorney, Agent, or Firm*—Armstrong, Nikaido, Marmelstein & Kubovcik

[57] ABSTRACT

Methylisobutylketone is produced from acetone in a high yield with a good selectivity through one-step reaction by contacting acetone together with at least one of water and hydrogen with an element of Group VIII of the periodic table, a halogen and a phosphorus compound as a catalyst under a super atmospheric pressure in a carbon monoxide atmosphere.

15 Claims, No Drawings

PROCESS FOR PRODUCING METHYLISOBUTYLKETONE

This invention is a novel process for producing methylisobutylketone from acetone, and more particularly to a process for producing methylisobutylketone from acetone through one-step reaction in the presence of an element of Group VIII of the periodic table, a halogen and a phosphorus compound as a catalyst under a superatmospheric pressure in a carbon monoxide atmosphere according to the following reaction formula:

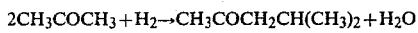

$$2CH_3COCH_3 + H_2 \rightarrow CH_3COCH_2CH(CH_3)_2 + H_2O$$

Heretofore, methylisobutylketone has been produced from acetone according to a process comprising a first step of condensing two molecules of acetone into diacetone alcohol in the presence of barium hydroxide, etc. as a catalyst, a second step of dehydrating diacetone alcohol into mesityl oxide in the presence of sulfuric acid, etc. as a catalyst, and a third step of hydrogenating mesityl oxide into methylisobutylketone in the presence of a nickel or copper catalyst, where a considerable amount of methylisobutylcarbinol is by-produced.

The conventional process based on such compricated steps is hardly a commercially satisfactory process for producing isobutylketone.

On the other hand, attempts have been so far made to synthesize methylisobutylketone by reaction of acetone with hydrogen through one-step reaction in the presence of copper or nickel in the form of metal or oxide (German Laid-open Patent Application (DOS) No. 2022365), palladium and chrome on an inert carrier (U.S. Pat. No. 3379766), a strong acid cation exchanger and a hydrogenation catalyst (German Pat. (DAS) No. 1193931) and synthetic zeolite or silicic acidalumina and palladium carbon (German Laid-open Patent Application (DOS) No. 1936203) according to the above-mentioned reaction formula. However, these attempts are not satisfactory in yield and selectivity.

As a result of an extensive study of overcoming various disadvantages as described above, the present inventors have found that methylisobutylketone can be synthesized from acetone in high yield with a high selectivity through one-step reaction in the presence of an element of Group VIII of the periodic table, a halogen and a phosphorus compound as a catalyst under a superatmospheric pressure in a carbon monoxide atmosphere, and have established the present invention.

In the present invention, the element of Group VIII of the periodic table includes iron, cobalt, nickel, ruthenium, rhodium, palladium, osmium, etc., and above all, cobalt and rhodium are distinguished. The applicable forms of the element include simple substances and compounds, which are used as dispersed or dissolved in a reaction system. The applicable compounds include oxides, hydroxides, organic acid salts, carbonates, sulfides, sulfates, nitrates, halides, organic metal complexes, carbonylates, etc.

In the present invention, the halogen means iodine and bromine, and the applicable mode of the halogen are halogen molecules, and such halogen compounds as halogenic acids, or metal salts of halogenic acids. Iodine and bromine can be used together at the same time.

When the applicable mode of the element of Group VIII is an iodide or bromide, the halogen can be added to a reaction system or not. That is, when the iodide or bromide of the element of Group VIII is used, it is not always necessary to add the halogen to the reaction system.

In the present invention, various phosphorus compounds can be effectively utilized. Particularly, alkylphosphine such as tributylphosphine, triphenylphosphine, diphenylphosphine, phenylphosphine, etc., alkylphosphine oxide such as tributylphosphine oxide, diamylphosphine oxide, triethylphosphine oxide, trimethylphosphine oxide, triphenylphosphine oxide, etc., alkylphoshponium salt such as tetraphenylphosphonium bromide, tetraphenylphosphonium iodide, etc. and alkylphosphine sulfide such as trimethylphosphine sulfide, triphenylphosphine sulfide, etc. is effective.

The amount of the catalyst to be used for effectively carrying out the reaction according to the present invention is 0.2–200 milligram-atoms, preferably 5–50 milligram-atoms of an element of Group VIII per mole of acetone; 0.1–500 milligram-atoms, preferably 5–100 milligram-atoms of a halogen per mole of acetone; and 0.1–500 milligram-atoms, preferably 5–200 milligram-atoms of a phosphorus compound in terms of phosphorus atom per mole of acetone.

The reaction proceeds even below the respective lower limits of the above-mentioned ranges, but the reaction rate is retarded, whereas amounts above the respective upper limits of the above-mentioned ranges have no adverse effect upon the reaction, but are not economical, and thus the above-mentioned ranges are practically satisfactory.

According to the present invention, reaction can be carried out without using a solvent, but a solvent can be used to make better dispersion or dissolution of a catalyst, depending upon the species of the catalyst, to make better recovery of a catalyst after the reaction and also to suppress side reaction. Applicable solvents include various amides, nitriles, aliphatic and aromatic hydrocarbons, organic acid esters, etc.

In the present invention, the presence of carbon monoxide is essential for functioning the catalyst to proceed with the reaction. A necessary carbon monoxide partial pressure is partically in a range of 50 to 200 kg/cm$^2$. The reaction proceeds below the lower limit of the above-mentioned range, but the reaction rate is retarded, whereas the partial pressure above the upper limit of the above-mentioned range has no adverse effect upon the reaction, but is not economical.

In the reaction according to the present invention, the presence of hydrogen is essential, as described in the above-mentioned reaction equation, but when there is water in the reaction system, the reaction can proceed without supplying hydrogen to the reaction system. That is, it seems that, if there are carbon monoxide and water in the reaction system, water shift reaction takes place to some extent under the reaction conditions of the present invention, forming hydrogen. It is a great advantage of the present invention that the reaction can proceed satisfactorily under such hydrogen partial pressure. Water is also formed by the reaction, and thus only a small amount of water must be present in the reaction system at the start of reaction. However, the presence of water also has an effect of improving the selectivity, and thus it is preferable to add water to the reaction system, even if hydrogen is supplied to the reaction system. In case of both water and hydrogen being supplied, an effect of preventing consumption of carbon monoxide due to the above-mentioned water shift reaction is obtained. When the hydrogen is supplied to the reaction system, a satisfactory hydrogen partial pressure is not more than 200 kg/cm$^2$, preferably not more than 150 kg/cm$^2$. If the hydrogen partial pressure is too high, by-production of isopropanol from acetone and other side reactions are more liable to take place, and thus too high a hydrogen partial pressure is not preferable.

In the present invention, an inert gas such as argon, nitrogen, carbon dioxide, methane, ethane, etc. can be mixed into carbon monoxide and hydrogen, so far as carbon monoxide and hydrogen can be maintained in the above-mentioned ranges of the partial pressures.

The amount of water to be added to the reaction system is not more than 2 moles, preferably not more than 1 mole per mole of acetone. The amount above 2 moles of water per mole of acetone can also have the effect of improving the selectivity, but is not preferable, because the reaction rate is retarded.

The reaction according to the present invention is carried out generally in a range of 150° to 350° C., though dependent upon the species of a catalyst to be used and other reaction conditions. The reaction proceeds even at a lower temperature, which is however not practical in the reaction rate, whereas too high a temperature is not preferable, because side reactions are more liable to take place.

When the present invention is carried out under the foregoing conditions, methylisobutylketone can be obtained from acetone through one-step reaction, and thus the present invention can provide a commercially useful, novel process for producing methylisobutylketone.

The present process can be carried out batchwise or continuously.

The present invention will be described in detail below, referring to Examples.

EXAMPLE 1

10 g of acetone, 2 g of cobalt bromide (CoBr$_2$.6H$_2$O), 2 g of triphenylphosphine and 5 g of N-methyl-2-pyrrolidone were added to a shaking-type, stainless steel autoclave having a net capacity of 100 ml, and a mixed gas of hydrogen and carbon monoxide (molar ratio of H$_2$/CO=1) were introduced thereto under a pressure of 180 kg/cm$^2$ gage, and reaction was carried out at 250° C. for two hours. As a result, a selectivity to methylisobutylketone of 75% was obtained with an acetone conversion of 48.6% by mole. In addition, isopropanol, methylpentylketone, diisobutylketone, mesityl oxide, etc. were formed as by-products.

EXAMPLE 2

10 g of acetone, 1.5 g of cobalt iodide (CoI$_2$), 2 g of tributylphosphine, and 2 g of water were added to the same autoclave as used in Example 1, and a mixed gas of hydrogen and carbon monoxide (H$_2$/CO=1 by mole) was introduced thereto under a pressure of 180 kg/cm$^2$ gage. Reaction was carried out at 250° C. for three hours. As a result, a selectivity to methylisobutylketone of 86.5% was obtained with an acetone conversion of 55% by mole. In addition, the same by-products as in Example 1 were formed.

EXAMPLE 3

Reaction was carried out in the same manner and under the same conditions as in Example 1, except that only carbon monoxide (CO) was introduced thereto under a pressure of 150 kg/cm$^2$ gage in place of the mixed gas. As a result, a selectivity to methylisobutylketone of 90.3% was obtained with an acetone conversion of 40.2% by mole. In addition, the same by-products as in Example 1 were formed.

EXAMPLE 4

10 g of acetone, 1.5 g of rhodium chloride (RhCl$_3$), 1 g of iodine, 2 g of tributylphosphine, and 2 g of water were added to the same autoclave as used in Example 1, and a mixed gas of hydrogen and carbon monoxide (H$_2$/CO=1 by mole) was introduced thereto under a pressure of 180 kg/cm$^2$ gage. Reaction was carried out at 250° C. for two hours. As a result, a selectivity to methylisobutylketone of 80.2% was obtained with an acetone conversion of 28% by mole. In addition, isopropanol and mesityl oxide were formed as by-products.

EXAMPLE 5

10 g of acetone, 1.5 g of cobalt acetate ((CH$_3$CO$_2$)$_2$Co.4H$_2$O), 2.0 g of potassium iodide, 1.5 g of tributylphosphine, and 2 g of water were added to the same autoclave as used in Example 1, and a mixed gas of hydrogen and carbon monoxide (H$_2$/CO=0.11 by mole) was introduced thereto under a pressure of 200 kg/cm$^2$ gage. Reaction was carried out at 200° C. for 2 hours. As a result, a selectivity to methylisobutylketone of 91.3% was obtained with an acetone conversion of 15.0% by mole.

EXAMPLE 6

10 g of acetone, 2.0 g of cobalt carbonyl (Co$_2$(CO)$_8$), 1.5 g of iodic acid, 2.0 g of tributylphosphine oxide, and 2 g of water were added to the same autoclave as used in Example 1, and a mixed gas of hydrogen and carbon monoxide (H$_2$/CO=0.2 by mole) was introduced thereto under a pressure of 180 kg/cm$^2$ gage. Reaction was carried out at a temperature of from 140° C., gradually elevated to 320° C. for 0.5 hours. As a result, a selectivity to methylisobutylketone of 98.4% was obtained with an acetone conversion of 12.7% by mole.

EXAMPLE 7

10 g of acetone, 2.0 g of nickel nitrate (Ni(NO$_3$)$_2$.6H$_2$O), 1.5 g of iodine, 2.5 g of tributylphosphine sulfide, and 2 g of water were added to the same autoclave as used in Example 1, and a mixed gas of hydrogen and carbon monoxide (H$_2$/CO=1 by mole) was introduced thereto under a pressure of 200 kg/cm$^2$ gage. Reaction was carried out at 280° C. for 2 hours. As a result, a selectivity to methylisobutylketone of 76.0% was obtained with an acetone conversion of 32.5% by mole.

EXAMPLE 8

10 g of acetone, 1.0 g of ruthenium chloride (RuCl$_3$), 0.5 g of cobalt chloride (CoCl$_2$), 1.0 g of iodine bromide, 2.5 g of tributylphosphine, and 2 g of water were added to the same autoclave as used in Example 1, and a mixed gas of hydrogen and carbon monoxide (H$_2$/CO=0.66 by mole) was introduced thereto under a pressure of 200 kg/cm$^2$ gage. Reaction was carried out at 260° C. for 2 hours. As a result, a selectivity to methylisobutylketone of 89.2% was obtained with an acetone conversion of 35.0% by mole.

What is claimed is:

1. A process for producing methylisobutylketone, which comprises contacting acetone with at least one member selected from the group consisting of water and hydrogen under superatomspheric pressure and under a carbon monoxide atmosphere using: (a) an element of Group VIII of the periodic table, said element being present as a simple substance, an oxide, a hydroxide, a salt, an organic metal complex or a carbonyl; and (b) a halogen selected from the group consisting of iodine and bromine, said halogen being present as elemental halogen, a halogenic acid or a metal salt of a halogenic acid; and (c) a phosphorus compound, said phosphorus compound being present as an alkylphosphine, an alkylphosphine oxide, an alkyl phosphonium salt, or an alkylphosphine sulfide as catalyst at a temperature effective for forming methylisobutylketone, the catalyst's components being present in amounts effective for forming methylisobutylketone.

2. A process according to claim 1, wherein the carbon monoxide has a partial pressure of 50 to 200 $kg/cm^2$.

3. A process according to claim 1, wherein the hydrogen has a partial pressure of not more than 200 $kg/cm^2$.

4. A process according to claim 1, wherein the water is in an amount of not more than 2 moles per mole of the acetone.

5. A process according to claim 1, wherein the element of Group VIII of the periodic table is iron, cobalt, nickel, ruthenium, rhodium, palladium, orosmium.

6. A process according to claim 5, wherein the element of Group VIII of the periodic table is cobalt or rhodium.

7. A process according to claim 1 wherein the element of Group VIII of the periodic table is present as a salt selected from the group consisting of organic salts, carbonates, sulfides, sulfates, nitrates, and halides.

8. A process according to claim 1, wherein the elements of Group VIII of the periodic table and the halogen are in the form of at least one of iodide and bromide of the element of Group VIII of the periodic table.

9. A process according to claim 1, wherein the alkylphosphine is tributylphosphine, triphenylphosphine, diphenylphosphine, or phenylphosphine, the alkylphosphine oxide is tributylphosphine oxide, diamylphosphine oxide, triethylphosphine oxide, trimethylphosphine oxide or triphenylphosphine oxide, the alkylphosphonium salt is tetraphenylphosphonium bromide, or tetraphenylphosphonium iodide, and the alkylphosphine sulfide is trimethylphosphine sulfide or triphenylphosphine sulfide.

10. A process according to claim 1, wherein 0.2-200 milligram-atoms of the element of Group VIII of the periodic table, 0.1-500 milligram-atoms of the halogen, and 0.1-500 milligram-atoms of the phosphorus compound in terms of phosphorus atom are used per mole of acetone.

11. A process according to claim 1, wherein an inert gas is contained in the carbon monoxide and the hydrogen.

12. A process according to claim 11, wherein the inert gas is argon, nitrogen, carbon dioxide, methane or ethane.

13. A process according to claim 1, wherein not more than 2 moles of the water is used per mole of the acetone.

14. A process according to claim 1, wherein the reaction is carried out in a range of 150°–350° C.

15. A process according to claim 1, wherein the reaction is carried out batchwise or continuously.

* * * * *